(12) United States Patent
Derby (10) Patent No.: US 9,766,192 B2
(45) Date of Patent: Sep. 19, 2017

(54) BROADBAND CIRCUIT FOR NUCLEAR MAGNETIC RESONANCE

(71) Applicant: One Resonance Sensors, LLC, San Diego, CA (US)

(72) Inventor: Kevin Derby, Carlsbad, CA (US)

(73) Assignee: One Resonance Sensors, LLC, San Diego, CA (US)

( * ) Notice: Subject to any disclaimer, the term of this patent is extended or adjusted under 35 U.S.C. 154(b) by 596 days.

(21) Appl. No.: 14/201,222

(22) Filed: Mar. 7, 2014

(65) Prior Publication Data

US 2015/0253396 A1    Sep. 10, 2015

(51) Int. Cl.
  *G01N 24/08* (2006.01)
  *G01R 33/28* (2006.01)
  *G01R 33/58* (2006.01)
  *G01R 33/36* (2006.01)

(52) U.S. Cl.
  CPC ........... *G01N 24/082* (2013.01); *G01N 24/08* (2013.01); *G01R 33/28* (2013.01); *G01R 33/3642* (2013.01); *G01R 33/583* (2013.01)

(58) Field of Classification Search
  CPC .... G01N 24/082; G01N 24/08; G01R 33/583; G01R 33/3562; G01R 33/28
  See application file for complete search history.

(56) References Cited

U.S. PATENT DOCUMENTS

| | | |
|---|---|---|
| 4,684,895 A | 8/1987 | Misic |
| 4,739,268 A | 4/1988 | Fox |
| 5,451,873 A | 9/1995 | Freedman et al. |
| 5,500,591 A | 3/1996 | Smith et al. |
| 5,698,979 A | 12/1997 | Taicher et al. |

(Continued)

FOREIGN PATENT DOCUMENTS

WO    2013077922 A3    8/2013

OTHER PUBLICATIONS

Specification Sheet for Bourns (TM) CM45 Series SMT Chip Inductors; https://www.bourns.com/pdfs/cm.pdf.*

(Continued)

*Primary Examiner* — David M Gray
*Assistant Examiner* — Laura Roth
(74) *Attorney, Agent, or Firm* — Procopio Cory Hargreaves and Savitch LLP; Pattric Rawlins (57) ABSTRACT

A device and system for generating a broadband excitation signal and corresponding excitation field to a substance under test in an NMR system is presented. The excitation signal is generated, according to a broadband transmitter, to a coil in the NMR system. A corresponding broadband receiver is also presented that acquires a response signal resulting from a response field emanating from the substance under test. Neither the transmitter nor the receiver require that the frequency of operation be determined according to a particular configuration of electrical devices to determine a resonance characteristic that tunes to a particular operational frequency. Rather, the operational frequency is determined according to control and driver devices triggered according to command and control signals in the case of the transmitter, and according to reactive elements, that are not configured as a tuned circuit, in the case of the receiver.

18 Claims, 3 Drawing Sheets

(56) References Cited

U.S. PATENT DOCUMENTS

| | | | |
|---|---|---|---|
| 6,054,858 | A | 4/2000 | Dumoulin et al. |
| 6,392,408 | B1 | 5/2002 | Barrall et al. |
| 7,026,814 | B2 | 4/2006 | Bordon et al. |
| 7,355,402 | B1 | 4/2008 | Taicher et al. |
| 7,759,938 | B2 | 7/2010 | Prado et al. |
| 2009/0096447 | A1* | 4/2009 | Prance ............... G01R 33/323 324/307 |
| 2010/0090698 | A1 | 4/2010 | Blumich et al. |
| 2010/0141255 | A1 | 6/2010 | Adolphi et al. |
| 2011/0109310 | A1 | 5/2011 | Hornung |
| 2013/0200899 | A1 | 8/2013 | Yi et al. |
| 2013/0234706 | A1 | 9/2013 | Mandal et al. |
| 2015/0177348 | A1* | 6/2015 | Peng .................... G01N 24/08 324/309 |

OTHER PUBLICATIONS

International Search Report and Written Opinion received in PCT/US2015/019289, mailed May 29, 2015, 10 pages.
International Search Report and Written Opinion received in PCT/US2012/053575, dated May 13, 2013, 9 pages.
First Saudi Arabian Office Action received in 114350371, 5 pages.
Extended European Search Report received in 12851906.3, dated Mar. 24, 2015, 10 pages.
Burnett et al. "Signal processing considerations in NMR detection of liquid explosives," Proceedings of SPIE, vol. 1824, Nov. 16, 1992, 11 pages.
Espy et al. "Progress on Detection of Liquid Explosives Using Ultra-Low Field MRI," IEEE Transactions on Applied Superconductivity, vol. 21, No. 3, Jun. 1, 2011, 4 pages.
Gradisek et al. "NMR-Based Liquid Explosives Detector," Applied Magnetic Resonance, vol. 38, No. 4, Jun. 18, 2010, 9 pages.
Gudmundson et al. "Detection and Classification of Liquid Explosives Using NMR," Acoustics, Speech and Signal Processing, Apr. 19, 2009, 4 pages.
King et al. "Development and evaluation of magnetic resonance technologies, particularly NMR, for detection of explosives," Applied Magnetic Resonance, vol. 25, No. 3-4, Sep. 1, 2004, 31 pages.
Kumar, "Liquid-contents verification for explosives, other hazards, and contraband by magnetic resonance," Applied Magnetic Resonance, vol. 25, No. 3-4, Sep. 1, 2004, 13 pages.
Kumar et al. "Screening seated bottles for liquid explosives," Proceedings of SPIE, vol. 2934, Jan. 29, 1997, 12 pages.
Kumar et al. "Magnetic-resonance-based system for chemical agent screening," Proceedings of SPIE, vol. 5071, Sep. 23, 2003, 12 pages.
Mauler et al. "Identification of Liquids Encountered in Carry-on-Luggage by Mobile NMR," Explosives Detection Using Magnetic and Nuclear Resonance Techniques, 2009, 13 pages.

* cited by examiner

BROADBAND CIRCUIT FOR NUCLEAR MAGNETIC RESONANCE

CROSS-REFERENCE TO RELATED APPLICATION

This present application is related to U.S. patent application Ser. No. 14/201,340, filed on Mar. 7, 2014, which is hereby incorporated by reference in its entirety.

BACKGROUND

Field

Aspects of the present invention generally relate to nuclear magnetic resonance (NMR) and, more particularly, to broadband operation of an NMR system.

Related Art

NMR systems are used to analyze material properties of a substance under test by applying an excitation magnetic field of known characteristics as stimulus to the substance during an excitation phase and by detecting a resulting magnetic field during a response phase. The detected signal is processed and analyzed to determine the material property of interest. Typical NMR systems are narrow-band systems, in which the system is designed to operate over a narrow range of frequencies. The narrowness of this range may be due to an electrically tuned circuit that is used to detect the response magnetic field produced by the sample, and may further be due to electrically tuned circuits in the electronics used to receive and process the response signal, electrically tuned circuits in the electronics use to excite the sample, and/or electrically tuned circuitry that couples the excitation and reception electronics to the circuit that detects the response magnetic fields due to the sample.

The tuning of frequencies in NMR systems have meant that analyses are limited in accuracy and energy coupling to the substance under test by how well the tuning and selection of the operational frequency matches the material characteristics of the substance. A further limitation has been the configuration of circuitry coupling the coil to the transmitter and receiver during the respective excitation and response phases. For example, active switches may be used to couple either the transmitter or the receiver to the coil during a transmit mode or receive mode respectively. The switching of the corresponding impedance of the transmitter and receiver to and from the coil result in a continual modulation of the impedance characteristics of this tuned circuit, which determines the operational frequency of the excitation or response modes. These factors collectively contribute to limitations in the effectiveness and accuracy of NMR analyses.

SUMMARY

The following presents a simplified summary of one or more embodiments in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments in a simplified form as a prelude to the more detailed description that is presented later.

A broadband transmitter is utilized within an NMR system to provide stimulus signals to an NMR coil. Within the broadband transmitter, a controller and driver can be configured to produce stimulus signals to the NMR coil across a broad range of frequencies. Since there is no requirement in the present approach for a resonance between the coil and a further electrical component in the transmitter, the transmitter may drive the coil at a stimulus signal frequency that is not determined by a tuned circuit. A tuned-circuit approach would limit the operational frequency to a narrow band of frequencies and do so according to a particular configuration of electrical components. Instead, the stimulus frequency is determined by the frequency of the control signals coming from the controller and the corresponding frequency of the coil configuration signal coming from the driver.

A broadband receiver is also utilized within the present NMR system to acquire a response signal resulting from a substance under test. Concepts similar to those described above in regard to the broadband transmitter are incorporated within the broadband receiver to effect a similar wide range of frequencies over which the receiver may operate to acquire response signals.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

Figure 1:
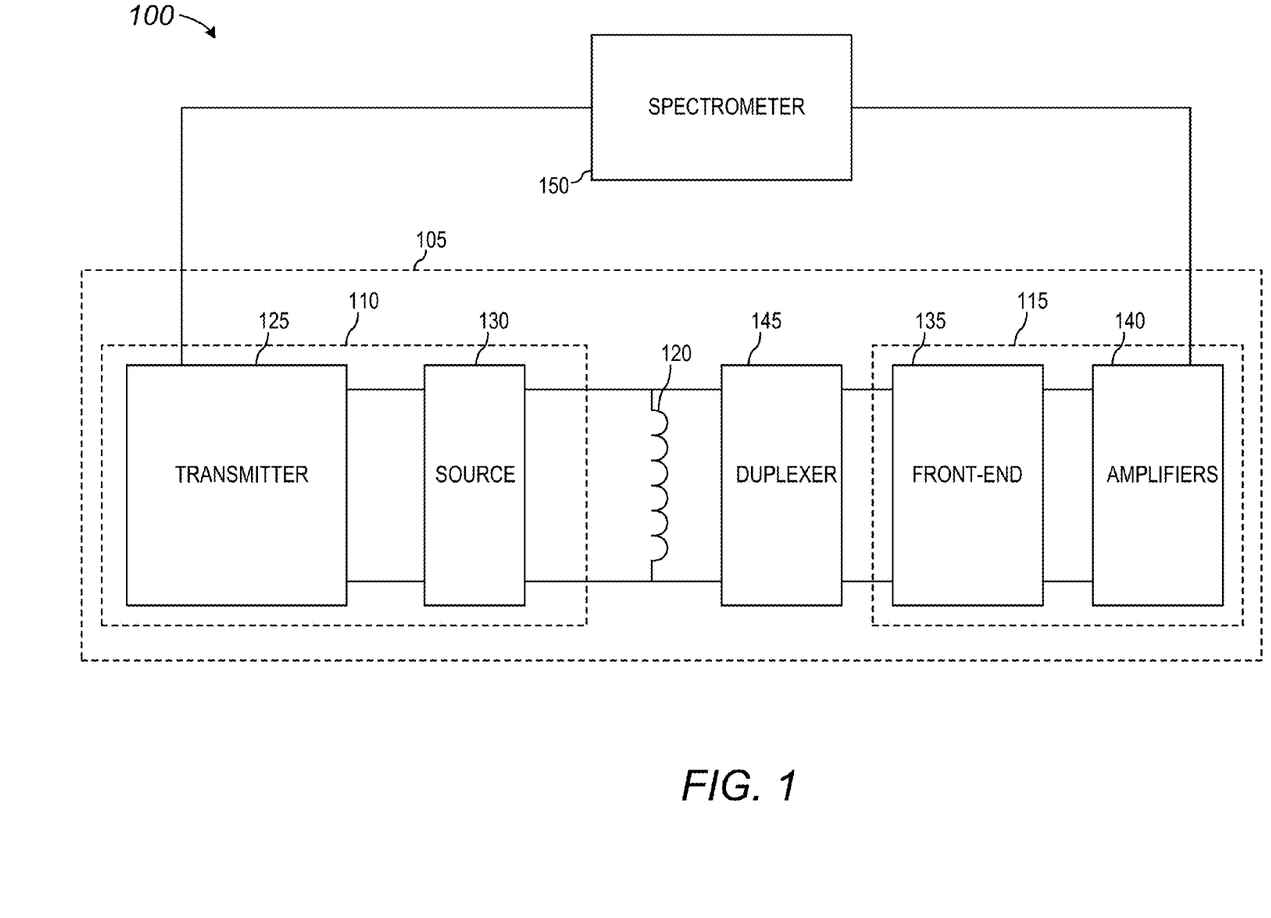
FIG. 1 is a block-level schematic diagram illustrating a broadband magnetic resonance system, according to an example embodiment.

FIG. 1 is a block-level schematic diagram illustrating a broadband magnetic resonance system 100, according to an example embodiment. The broadband magnetic resonance system 100 can be used in analyzing substances to determine their material properties. The broadband magnetic resonance system 100 can be used to provide an excitation magnetic field to a substance under test. According to nucleic material properties, the excitation field may excite the nuclei of certain materials into magnetic resonance. Once the excitation field is halted, the energy stored in the magnetic moments of the nuclei may give off a resulting magnetic field that is characteristic of the material's properties. The magnetic field is generated by the material nuclei during a response phase.

The broadband magnetic resonance system 100 may include a broadband nuclear magnetic resonance device 105 that includes a broadband transmitting device 110 and a broadband receiver 115. The broadband transmitting device 110 can be communicatively coupled to a coil 120 and used to provide a stimulus signal to generate a stimulus field in the coil 120. The stimulus field is the excitation field applied to the substance under test. The broadband receiver 115 may be used to acquire response signals corresponding to the magnetic field produced by the substance under test. The stimulus signal may be generated by the broadband transmitting device 110 during a transmit mode and response signals corresponding to the response field can be received by the broadband receiver 115 during a receive mode. The transmit mode and the receive mode are mutually exclusive (e.g., nonoverlapping states of the broadband transmitting device 110 and the broadband receiver 115) since the corresponding excitation field and response field are mutually exclusive in order to analyze the material properties of the substance under test.

The broadband transmitting device 110 can include a broadband transmitter 125 and a current source 130, for example. The current source 130 may be communicatively coupled between the broadband transmitter 125 and the coil 120. The current source 130 can include voltage regulation and isolation components (not shown) that may be used to control the characteristics of the stimulus signal and isolate the broadband transmitter 125 from the broadband receiver 115 during the receive mode. The current source 130 can receive the stimulus signal from the broadband transmitter 125 and generate a regulated signal, such as a regulated output current, for example, to the coil 120. The current source 130 can include an isolation section (not shown) between a regulation section and the coil 120. The broadband transmitter 125 may be communicatively coupled to the coil 122 to provide the stimulus signal for generating the stimulus field in the coil 120. The stimulus signal is generated by the broadband transmitter 125 during the transmit mode.

The broadband receiver 115 can include a receiver front end 135 and an amplifiers section 140. The receiver front-end 135 can be communicatively coupled to the coil 120 and be configured to receive the response signal corresponding to the response field emitted by the substance under test. The response signal may be received during the receive mode. The receiver front-end 135 can be configured to adapt to the characteristics of the response signal. For example, the receiver front-end 135 includes a reactive circuit element (discussed below) that may be configured to respond to the voltage and current characteristics that the coil 120 may provide as the response signal. With only a reactive element at the receiver front-end 135, no tuning is required in the broadband receiver 115 to accommodate a broad range of frequency responses that can make up the response signal. Once the receiver front-end 135 has received the response signal, the detected signal is provided to the amplifiers section 140. The amplifiers section 140 may include active amplifying elements that boost, or amplify, the strength of the detected response signal and provide the amplified signal as an output to further elements of the broadband magnetic resonance system 100.

The broadband receiver 115 and the broadband transmitter 125 are to be isolated from one another during the transmit mode and the receive mode. This may generally be done according to control of the respective transmit and receive states of the system to ensure that the transmit state in the receive state do not overlap. However, where the broadband transmitter 125 and the broadband receiver 115 are continuously coupled through a passive duplexer, additional isolation may be provided within the duplexer configuration to ensure that the stimulus signal coming from the broadband transmitting device 110 does not excessively overload the broadband receiver 115 during the transmit mode. That is, the broadband receiver 115 maybe overloaded to a certain extent. However, the broadband receiver 115 is not allowed to be so excessively overloaded that damage occurs. Accordingly, a passive duplexer 145 is communicatively coupled between the coil 120 and the broadband receiver 115, and is configured to isolate the broadband receiver 115 during the transmit mode.

Some NMR systems utilize a duplexer for similar reasons to those stated above, but do so with active devices. For example an active duplexer may include switches composed of transistors (often field effect transistors) connected in series between the coil and the receiver. By opening and closing the series connected transistors, the receiver may be isolated from the coil during the transmit mode. However, the transistors require additional drive and control circuitry to provide the control voltages to open and close the transistors and do so with appropriate timing with respect to the transmit mode and the receive mode. A further limitation is the additional requirement that the reference ground to this circuitry and the switching transistors may not be the same as the reference ground of the NMR system. Establishing a correct ground reference can be required for proper biasing of the gate-to-source and gate-to-drain voltages of the series-connected field effect transistors (FETs) so that correct operation is maintained by the devices during the voltage excursion on the attached coil. This condition is met in duplexers so that the isolating effects of the transistors is effective during the entire transmit mode. If the proper gate voltage to the FETs is not maintained, the transistors can conduct and no longer provide isolation of the receiver from the coil. Providing proper control gate voltages can require that the drive and control circuitry be isolated from the switches.

The proper control gate voltage requirement is met in systems employing FET switches via the use of isolated signal transmission methods. The isolation of signal transmissions to the control and drive circuitry may be accomplished with optical isolators ('optoisolators') or magnetic transmission methods (e.g., requiring a transformer). The additional circuitry, control, timing, and signal isolation requirements all present additional steps that must be accomplished in order to provide duplexer operation according to the active devices approach. The requirements of the active device-based duplexer represent additional design effort, costs, and time to provide isolation of the receiver from the coil.

Most traditional NMR systems employ designs in which the coil impedance is transformed through a matching network to 50 Ohms. This enables relatively remote connection of the transmitter and receiver to the coil through a 50 Ohm transmission line, which is useful, particularly at high frequencies. In this case, a typical duplexer is often constructed using one or more sections of transmission line that represent an odd multiple of ¼ wavelength at the frequency interest, in conjunction with either passive diode pairs or an active PIN diode switch in shunt to ground. Although this method is effective, it is not a broadband technique due to the requirement of the specific transmission line length. There are methods for tuning duplexers at multiple frequencies, however the duplexer will still only operate at a discrete set of frequencies, as opposed to a true broadband device.

The passive duplexer 145, according to certain exemplary embodiments, includes passive devices (discussed below) that are continuously coupled between the coil 120 and the broadband receiver 115 during the transmit mode and the receive mode. No additional active devices require triggering or controlling during either the transmit mode or the receive mode in order for the passive duplexer 145 to provide isolation of the broadband receiver 115 from the coil 120. Accordingly, the passive duplexer 145 of the present exemplary embodiment, avoids the requirement for driving, controlling, designing, and purchasing the components necessary to effect the active duplexer of typical NMR systems.

The broadband magnetic resonance system 100 may also include a spectrometer 150 that can be connected between an output of the amplifiers section 140 and an input to the broadband transmitter 125. The spectrometer 150 may take in the amplified signal provided by the amplifier section 140 and perform various diagnostic and characterization methods on the amplified signal. A user of the broadband magnetic resonance system 100 may use a graphical user interface (GUI) to interact with the spectrometer 150 and direct an analysis of the substance under test to characterize various of the material properties according to the amplified received signal. In the course of directing analytical processes, the user may utilize the spectrometer 152 provide a command signal to the broadband transmitter 125. This command signal may be used to configure the stimulus signal (described above) generated by the broadband transmitting device 110 during the transmit mode.

Figure 2:
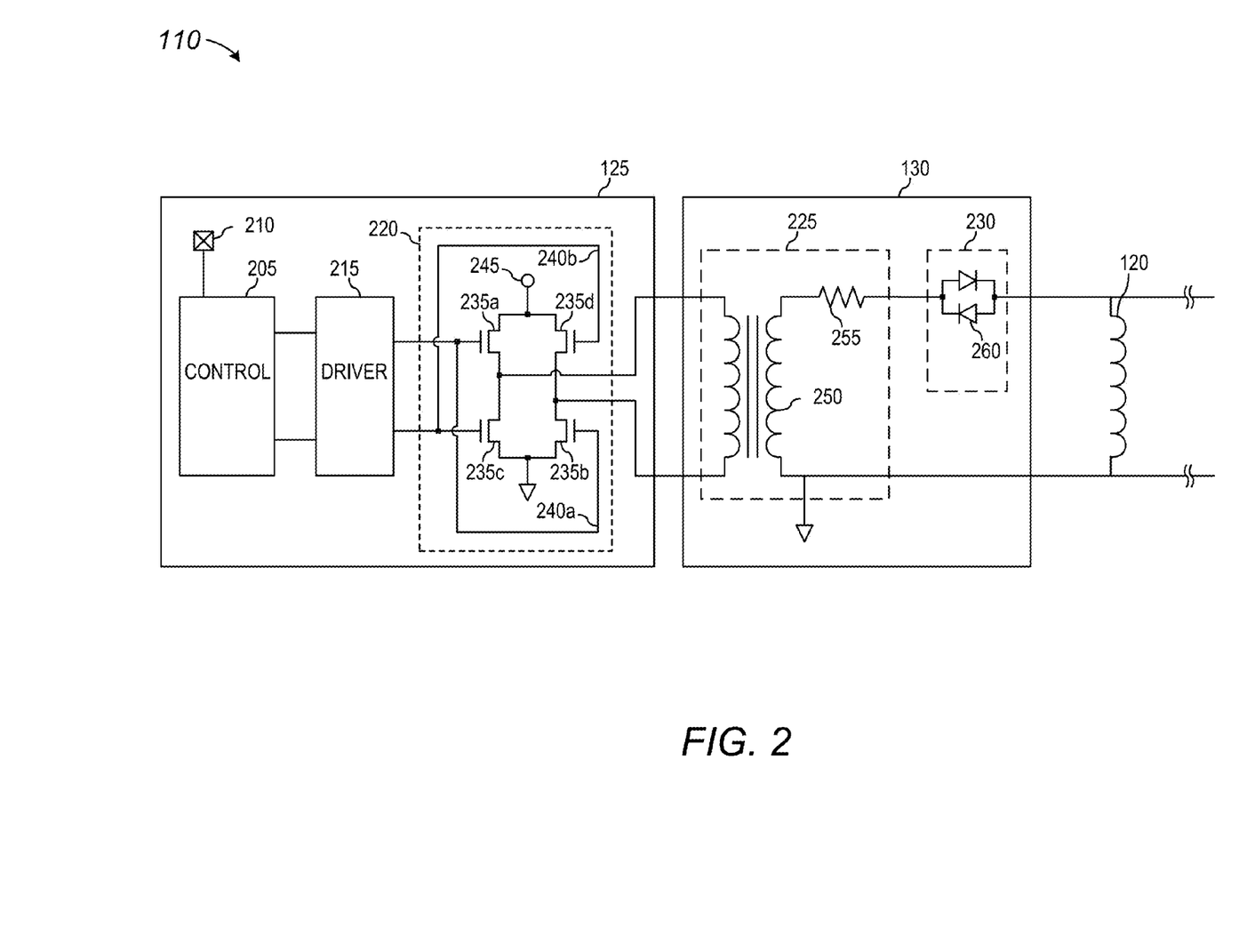
FIG. 2 is a device-level schematic diagram illustrating a broadband transmitting device, as may be used in example embodiments.

FIG. 2 is a device-level schematic diagram illustrating the broadband transmitting device 110 (FIG. 1) discussed above and as may be used according to example embodiments. The broadband transmitting device 110 is a "front-end" portion of the broadband magnetic resonance device 105 and includes the broadband transmitter 125 which is selectively configured to generate the stimulus signal during the transmit mode. The broadband magnetic resonance device 105 also includes the current source 130 which is communicatively coupled to the broadband transmitter 125. The broadband transmitter 125 includes a control circuit 205 coupled between an input terminal 210 and a driver circuit 215. The driver circuit 215 is communicatively coupled to a bridge circuit 220. The driver circuit 215 provides outputs that are coupled through the bridge circuit 220 to the current source 130.

The bridge circuit 220 may be implemented as an H-bridge including a first pair of bridge transistors 235a,b and a second pair of bridge transistors 235c,d. A first control line 240a couples from the driver circuit 215 to control inputs of the first pair of bridge transistors 235a,b and a second control line 240b couples from the driver circuit 215 to control inputs of the second pair of bridge transistors 235c,d. The driver circuit 215 provides a first component of the configuration signal through the first control line 240a to the first pair of bridge transistors 235a,b and a second component of the configuration signal through the second control line 240b to the second pair of bridge transistors 235c,d.

A command signal provided at the input terminal 210 can selectively configure the control circuit 205 to generate and provide the control signal to the driver circuit 215. The driver circuit is configured to provide a configuration signal corresponding to the control signal to the bridge circuit 220. When the first component of the configuration signal is applied to—and activates the first pair of bridge transistors 235a,b, a supply voltage from a power supply (not shown) may be introduced at a supply terminal 245 and the provided to a load within the current source 130 with a first polarity. In a complementary fashion, the second component of the configuration signal may activate the second pair of bridge transistors 235c,d to provide the supply voltage to the load with a second polarity, which is the inverse of the first polarity. The first component of the configuration signal is mutually exclusive (nonoverlapping) from the second component of the configuration signal. Only one conductive path, through either the first pair of bridge transistors 235a,b or the second pair of bridge transistors 235c,d, may be configured and activated at a time. The nonoverlapping characteristic is ensured according to the first and second component of the configuration signal.

In this way, a signal somewhere between a square wave and a sawtooth wave may be provided as the stimulus signal to the load depending on the resistive or inductive characteristics of the impedance of the load device. As the effects of the command signal propagate through the control circuit 205, the driver circuit 215, and the bridge circuit 220; the corresponding control signals, configuration signals, and stimulus signals are generated from the respective circuit elements. In this way, the command signal may cause the generation of the stimulus signal from the broadband transmitter 125, which may in turn be coupled to the coil 120 through the current source 130.

The current source 130 may include, for example, a regulator 225 coupled to an isolator 230 and the bridge circuit 220 in the broadband transmitter 125. The isolator 230 couples to the coil 120 at an output of the current source 130. The regulator 225 may include a step-up transformer 250 and a resistor 255. The step-up transformer 250 generates a voltage at a transformer output that is increased from the voltage introduced at the input of the transformer by an amount equal to the turns ratio. The step-up transformer 250 may have a turns ratio of 2:1, for example. The resistor 255 may be utilized as a current limiting element. A value of the resistor 255 may be selected, for example, to be about 50 Ohms.

The regulator 225 may be coupled in series to the isolator 230. The isolator 230 may be implemented by back-to-back parallel diodes 260, for example. Either one of the diodes in the back-to-back parallel diodes 260 will conduct when a sufficient magnitude of forward biasing voltage is introduced across its terminals. By symmetry, this is true for a voltage equal in magnitude to the forward bias voltage of either of the diodes. Conduction will occur with either a positive or negative polarity voltage of the forward biasing magnitude. When applied, such a magnitude of voltage will cause one or the other of the diodes to conduct. As long as the voltage difference between the two terminals of the isolator 230 is less than the forward biasing magnitude, the input and output terminals are isolated from one another.

The combination of the step-up transformer 250 in series with the resistor 255 forms a constant current source. The amplitude of the voltage applied to the step-up transformer 250 is substantially constant over time, yet the frequency varies according to the broadband transmitter 125. The voltage applied to the step-up transformer 250 is output from the bridge circuit 220. The first and second pair of bridge transistors 235a,b and 235c,d have substantial current-drive capability, but are limited in supplying a voltage amplitude according to the supply voltage available at the supply terminal 245. The step-up transformer 250 allows this current-drive capability of the first and second pair of bridge transistors 235a,b and 235c,d to be transformed into an effective elevated voltage capability. The relatively large amplitude voltage produced at the outputs of the step-up transformer 250 is provided to the resistor 255, which operates as a current limiter. The voltage input to the current source 130 is transformed, according to the step-up transformer 250 and the resistor 255, into a current-based signal through the coil 120.

Figure 3:
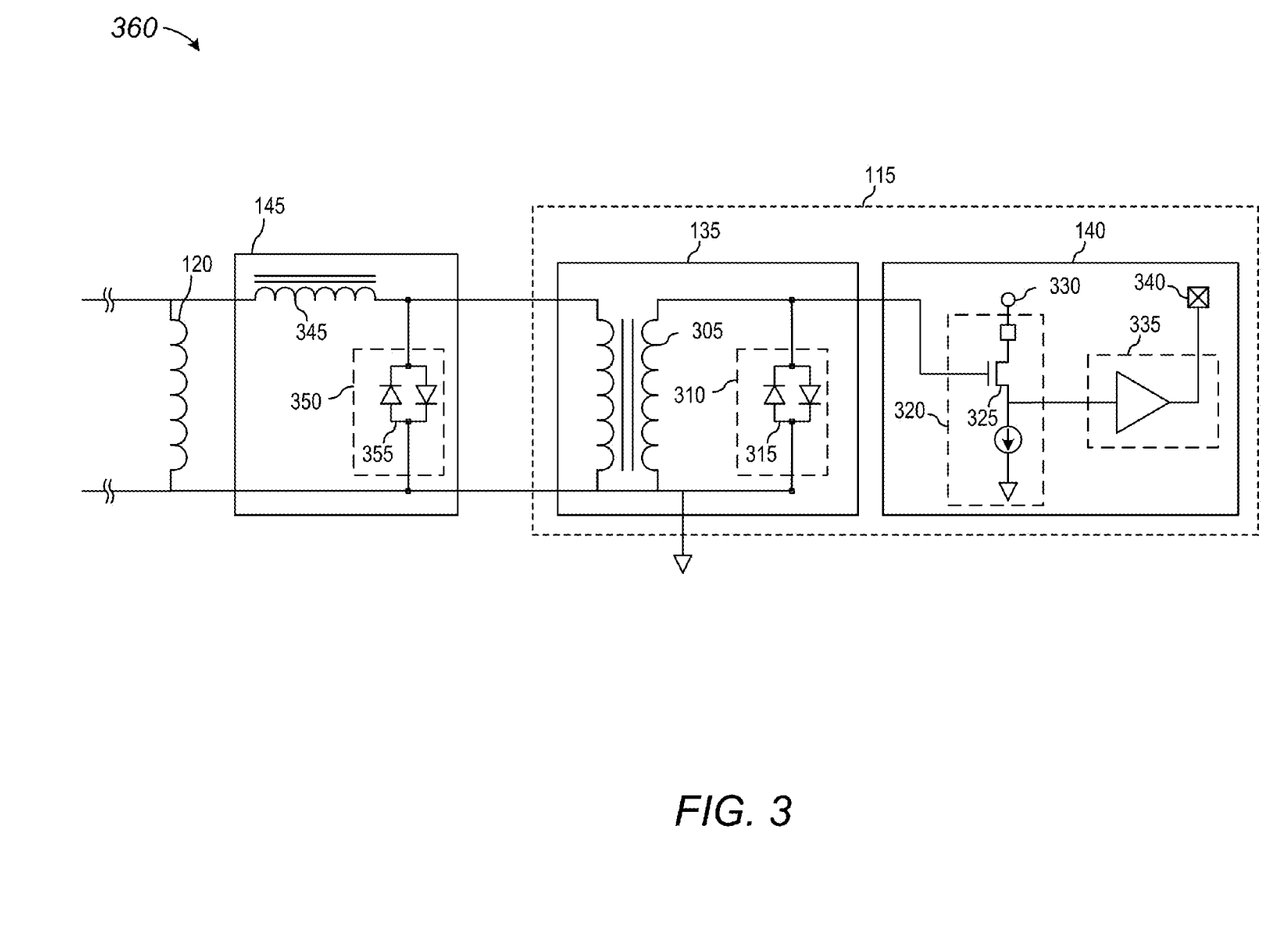
FIG. 3 is a device-level schematic diagram illustrating a broadband receiving device, as may be used in example embodiments.

The current source 130, which includes the regulator 225 in series with the isolator 230, provides a constant supply of current to the coil 120 that is stable across a broad range of frequencies. Accordingly, the current through the coil 120 is essentially independent of frequency. This constant current capability is effective over a range of frequencies where the impedance of the resistance 255 dominates over the reactance of the series combination of a leakage inductance of the step-up transformer 250, in conjunction with the inductance of the parallel combination of the coil 120 and a protection inductor 345. In practice, the transformer leakage inductance is small compared to the coil 120 and the protection inductor 345. The coil 120 and the protection inductor 345 are about 0.75 µH, for example. As long as the impedance of the resistor 255 (e.g., 50 ohms) dominates the reactance of the parallel combination of the coil 120 and the protection inductor 345 (e.g., 0.375 µH), the current from the current source 130 is substantially constant. Accordingly, the 3 decibel (dB) point is about 20 megahertz (MHz).

This stability in the supplied current reduces the tendency for a high degree of variation in coil current, and hence NMR excitation field, at high-frequencies. Stable operational currents may be introduced from the current source 130 to the coil 120 (i.e., as the stimulus signal) across a frequency range of about 2 MHz to 26 MHz, for example. The frequency of operation for the broadband transmitter 125 is determined by the operational frequency of the command signal, control circuit 205, driver circuit 215, and the bridge circuit 220. No further or additional tuning or resonant circuit is required to determine a particular operational frequency.

FIG. 3 is a device-level schematic diagram illustrating a broadband receiving device 360, as may be used in example embodiments. The broadband receiving device 360 is a "back-end" portion of the broadband magnetic resonance device 105 and includes the broadband receiver, the receiver front-end 135, the amplifiers section 140, and the passive duplexer 145.

The receiver front-end 135 includes a receiving step-up transformer 305 and a shunting device 310. The receiving step-up transformer 305 is coupled to the input of the broadband receiver 115. The receiving step-up transformer 305 is also communicatively coupled to the coil 120 and configured to receive a response signal corresponding to the response field induced in the coil 120 from the substance under test during the receive mode. To optimize performance, the receiving step-up transformer 305 may be configured, for example, to have high magnetizing inductance, a low series resistance, a high turns ratio, and low leakage inductance. The receiving step-up transformer 305 is configured according to a turns ratio to produce an output voltage as a portion of the input voltage. A turns ratio of 3:12, for example, may be utilized in the receiving step-up transformer 305. This would result in the output voltage being amplified by about a factor of four over the input voltage to the receiving step-up transformer 305. Performance of the receiving step-up transformer 305 may be further configured according to a ferrite core which may be, for example, a type 61 ferrite binocular core.

The shunting device 310 may include a second set of back-to-back parallel diodes 315 that operate substantially as discussed above. However, in the receiver front-end 135, the back-to-back parallel diodes 315 operate to clamp a voltage output from the receiving step-up transformer 305 to about one diode threshold, regardless of polarity. The magnitude of clamping voltage provided by the shunting device 310 may be on the order of 0.6-0.7 volts (V). Accordingly, the broadband receiver 115 utilizes the receiving step-up transformer 305 in the receiver front-end 135 to provide an output voltage about four times the magnitude of an input voltage to the amplifier section 140. However, the magnitude of the output voltage from the receiving step-up transformer 305 is clamped to about one diode threshold (positive or negative) from ground potential.

The amplifiers section 140 can include a preamplifier 320 having a transconductance device 325, for example, coupled between a receiver supply terminal 330 and ground. An amplifier 335 may be communicatively coupled between the preamplifier 320 and an output terminal 340. The transconductance device 325 may be selected for its control input terminal characteristics. This is due to the sensitive nature of how the impedance characteristics of the input terminal of the transconductance device 325 interrelate with the output characteristics of the receiving step-up transformer 305. The desired input characteristics of the transconductance device 325 may be met by field effect devices, such as a junction-field-effect-transistor (JFET) or a metal-semiconductor field-effect-transistor (MESFET). The MESFET may, for example, be used at higher frequencies and the JFET at lower frequencies. A MESFET fabricated from a gallium arsenide (GaAs) technology offers a low input capacitance and can be favored for high-frequency operation. However, the MESFET transconductance characteristics may suffer from inverse frequency (1/f) noise problems due to surface and channel traps introduced according to material layering characteristics inside the FET. These characteristics are substantial noise contributors at low frequencies. A peak in response of the broadband receiver 115 occurs due to the resonance of inductance seen by the input capacitance of the preamplifier 320. This effective inductance is due to the combination of the coil inductance, together with that of the protection inductor 345, stepped up through the effect of the transformer 305, in combination with the leakage inductance of the transformer itself. The peak in response of the broadband receiver 115 may be mitigated, for example, by adding a large value resistance from output to input of the amplifier 140. A large value resistor should be used to avoid impacting the noise performance through the current noise of the feedback resistor, which effectively appears at the amplifier input.

The "back-end" portion of the broadband magnetic resonance device 105 also includes the passive duplexer 145, which is coupled between the coil 120 and the receiving step-up transformer 305 in the broadband receiver 115. The passive duplexer 145 may include a protection inductor 345 coupled in series between an input and output of the duplexer and a duplexer shunt 350 coupled from the output to ground. The duplexer shunt 350 operates and is configured similarly to the shunting device 310 as described above in the receiver front-end 135 description. The duplexer shunt 350 may be implemented according to a third set of back-to-back parallel diodes 355.

Construction of the passive duplexer 145 (FIG. 3) includes a passive protection component, namely the protection inductor 345, and may also include the third set of back-to-back parallel diodes 355 in the duplexer shunt 350. The third set of back-to-back parallel diodes 355 are effectively coupled across the input terminals of the broadband receiver 115. One of the diodes in the third set of back-to-back parallel diodes 355 receives a forward biasing voltage during the transmitting phase and conducts current accordingly. The third set of back-to-back parallel diodes 355 is open during the receiving phase. The protection inductor 345 may have a value about equal to that of the coil 120, which may be on the order of 0.75 microhenrys (µH), for example.

Accordingly, the protection inductor 345 operates to limit surges of current from being introduced to other components as a result of operation of the broadband transmitter 125 (FIG. 1) during the transmit mode. For example, the protection inductor 345 operates to limit the current through the back-to-back parallel diodes 355 to their rated maximum and provide a splitting of the transmitter current between the coil 120 and the protection inductor 345. This current splitting forces a fraction of the current generated during transmission to flow through the coil and provide an NMR excitation field, rather than flowing exclusively through the diodes 355. Additionally, the duplexer shunt 350 operates to limit the voltage across the input terminals of the broadband receiver 115 to the magnitude of the forward bias voltage of one device threshold, or about 0.6-0.7V.

The impedance presented by the protection inductor 345 causes an attenuation of the signal-to-noise ratio (SNR) to the broadband receiver 115 of between about 1-2 dB. Further SNR attenuation may be mitigated by selecting an inductor with a higher Q than the coil. High Q inductors fabricated from larger numbers of turns and iron cores may be selected, for example, to improve the situation. The passive duplexer 145 also avoids having additional switching devices, the driver circuit, and the specialized signal transmission isolation schema required in the typical NMR system.

Those of skill in the art will appreciate that the various illustrative blocks and modules described in connection with the embodiments disclosed herein can be implemented in various forms. Some blocks and modules have been described above generally in terms of their functionality. How such functionality is implemented depends upon the design constraints imposed on an overall system. Skilled persons can implement the described functionality in varying ways for each particular application, but such implementation decisions should not be interpreted as causing a departure from the scope of the included embodiments. In addition, the grouping of functions within a module, block, or step is for ease of description. Specific functions or steps can be moved from one module or block without departing from the invention.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the present exemplary embodiments. Thus, it is to be understood that the description and drawings presented herein represent presently preferred embodiments and are therefore representative of the subject matter which is broadly contemplated. It is further understood that the scope of the present embodiments fully encompasses other embodiments that may become obvious to those skilled in the art and that the scope of the present embodiments is accordingly limited by nothing other than the appended claims.

What is claimed is:
1. A broadband magnet field control device comprising:
a transmitter selectively configured, according to a control signal, to generate a stimulus signal during a transmit mode, the transmitter including:
a control circuit selectively configured to generate the control signal;
a driver circuit communicatively coupled to the control circuit and configured to provide a configuration signal corresponding to the control signal; and
a bridge circuit communicatively coupled to the driver circuit and selectively configured to produce the stimulus signal according to a supply voltage and the configuration signal, wherein, according to the supply voltage, the bridge circuit generates the stimulus signal as an alternating voltage to the regulator, the alternating voltage is produced according to a first component of the configuration signal and a second component of the configuration signal;
a coil communicatively coupled to the transmitter and configured to generate a stimulus field corresponding to the stimulus signal, receive a response field, and correspondingly generate a response signal during a receive mode;
a regulator communicatively coupled to the transmitter and configured to generate an output current according to the stimulus signal;
an isolator coupled between the regulator and the coil, the isolator configured to electrically isolate the coil from the transmitter during the receive mode;
a receiver communicatively coupled to the coil and configured to receive the response signal during the receive mode; and
a duplexer communicatively coupled to the coil and the receiver, the duplexer configured to isolate the receiver during the transmit mode.

2. The device of claim 1, wherein the duplexer is a passive duplexer and includes an inductor and a shunting device.

3. The device of claim 2, wherein the inductor is a protection inductor coupled between a duplexer input and a duplexer output and the shunting device is coupled between the duplexer output and ground.

4. The device of claim 2, wherein the inductor is a protection inductor having a ferrite core and the shunting device includes a back-to-back parallel diodes circuit.

5. The device of claim 2, wherein the shunting device shunts a voltage exceeding a specified voltage limit at the inductor output, and further wherein the inductor is communicatively coupled in series between the coil and a receiver input.

6. The device of claim 1, wherein the driver circuit generates the first component of the configuration signal and the second component of the configuration signal as non-overlapping voltages.

7. The device of claim 1, wherein the regulator is configured to cause the transmitter to operate as a current source.

8. The device of claim 1, wherein the regulator is configured to generate a constant output current across an operational frequency range, wherein the operational frequency range spans from about 2 megahertz to about 26 megahertz.

9. The device of claim 1, wherein the regulator includes a step-up transformer coupled to a regulator input and a current limiting impedance coupled to a regulator output, further wherein a turns ratio of the step-up transformer is about two-to-one.

10. The device of claim 1, wherein the coil has a value of inductance of about 0.75 microhenries.

11. The device of claim 1, wherein the receiver includes a step-up transformer communicatively coupled to the receiver input and a preamplifier communicatively coupled to the step-up transformer output.

12. The device of claim 11, wherein the receiver includes a shunting device electrically coupled across the step-up transformer output, further wherein the shunting device is a voltage clamp limiting a voltage level on the step-up transformer output.

13. The device of claim 12, wherein a turns ratio of the step-up transformer is about four-to-one.

14. A broadband magnetic resonance system comprising:
a transmitter selectively configured, according to a control signal, to generate a stimulus signal during a transmit mode, the transmitter including:
    a control circuit selectively configured to generate the control signal;
    a driver circuit communicatively coupled to the control circuit and configured to provide a configuration signal corresponding to the control signal; and
    a bridge circuit communicatively coupled to the driver circuit and selectively configured to produce the stimulus signal according to a supply voltage and the configuration signal, wherein, according to the supply voltage, the bridge circuit generates the stimulus signal as an alternating voltage to the regulator, the alternating voltage is produced according to a first component of the configuration signal and a second component of the configuration signal;
a coil communicatively coupled to the transmitter and configured to generate a stimulus field corresponding to the stimulus signal, receive a response field, and correspondingly generate a response signal during a receive mode;
a regulator communicatively coupled to a transmitter output and configured to generate an output current according to the stimulus signal;
a passive duplexer communicatively coupled to the coil and the receiver, the passive duplexer configured to isolate the receiver during the transmit mode;
a receiver, including a preamplifier and an amplifier; and
a spectrometer communicatively coupled to the transmitter.

15. The system of claim 14, further comprising:
a power supply coupled to the bridge circuit and configured to generate the supply voltage, and
an isolator coupled between the regulator and the coil, the isolator configured to electrically isolate the coil from the transmitter during the receive mode;
wherein the regulator includes a step-up transformer coupled to a regulator input and a current limit impedance coupled to a regulator output;
wherein the passive duplexer includes an inductor and a shunting device; and
wherein the inductor is a protection inductor coupled between a duplexer input and a duplexer output and the shunting device is coupled between the duplexer output to ground.

16. The system of claim 15, wherein the control circuit is selectively configured to generate the control signal as a broadband signal.

17. The system of claim 14, wherein the transmitter is selectively configured, according to the control signal, to provide the stimulus signal to the regulator as an alternating radio frequency voltage.

18. The system of claim 15, wherein the transmitter is configured to generate the stimulus signal as a broadband signal.

* * * * *